(12) United States Patent
Sasaki et al.

(10) Patent No.: US 6,900,307 B1
(45) Date of Patent: May 31, 2005

(54) 2-AMINOPURINE DERIVATIVES

(75) Inventors: Shigeki Sasaki, Fukuoka (JP); Fumi Nagatsugi, Fukuoka (JP); Minoru Maeda, Fukuoka (JP)

(73) Assignee: Hisamitsu Pharmaceutical Co., Inc., Saga (JP)

( * ) Notice: Subject to any disclaimer, the term of this patent is extended or adjusted under 35 U.S.C. 154(b) by 102 days.

(21) Appl. No.: 10/129,301
(22) PCT Filed: Nov. 2, 2000
(86) PCT No.: PCT/JP00/07748
§ 371 (c)(1),
(2), (4) Date: Oct. 7, 2002
(87) PCT Pub. No.: WO01/34619
PCT Pub. Date: May 17, 2001

(30) Foreign Application Priority Data

Nov. 5, 1999 (JP) ............................................ 11/352150

(51) Int. Cl.⁷ ......................... C07H 21/00; C07H 19/20
(52) U.S. Cl. .................... 536/24.5; 536/26.7; 536/27.8; 514/44; 435/6; 435/91
(58) Field of Search ............................... 536/24.5, 26.7, 536/27.8; 514/44; 435/6, 91, 6.91

(56) References Cited

FOREIGN PATENT DOCUMENTS

| JP | 9-67392 | 3/1997 |
|---|---|---|
| JP | 9-124687 | 5/1997 |
| WO | WO 01/34619 A1 * | 5/2001 |

OTHER PUBLICATIONS

Nagatsugi et al. (I), "New Design of Artificial Nucleobases as Cross–Linking Agents based on the 'Prodrug' Strategy," *Abstracts, Symposium on Biofunctional Chemistry, 11*, 34–36 (1996); *JICST File on Science Technology and Medicine in Japan*, JST (Japan Science and Technology Agency) on STN as 970364213 (1997); only JICST abstract supplied.*

Nagatsugi et al. (II), "Synthesis and Cross–Linking of the Oligonucleotides Incorporating New Artifical Bases with Selective Reactivity to Cytidine," *Abstracts, Symposium on Biofunctional Chemistry, 12*, 189–191 (1997); *JICST File on Science Technology and Medicine in Japan*, JST on STN as 980230686 (1998); only JICST abstract supplied.*

Nagatsugi et al., 'Structural Analysis of Cross–linked Adducts With The Oligonucleotides Incorporating 2–Amino–6–Vinylpurin', Nucleic Acids Symposium Series No. 39, 1998 Oxford University Press, pp. 103–104.

Nagatsugi et al., 'Highly Effected and Selective Cross–Linking to Cytidine Based on a New Strategy for Auto–Activation Within a Duplex,' J. Am. Chem. Soc. 1999, 121, pp. 6753–6754, (Web Pub: Jul. 3, 1999).

Woolf, Tod M., 'Therapeutic Repair of Mutated Nucleic Acid Sequences', Nature Biotechnology, vol. 16, Apr. 1998, pp. 341–344.

Grant et al., 'Sequence–Specific Alkylation and Cleavage of DNA Mediated by Purine Motif Triple Helix Formation', Biochemistry 1996, 35, pp. 12313–12319, (Abstr Pub Sep. 15, 1996).

Shaw et al., 'Specific, High–Efficiency, Triple–Helix–Mediated Cross–Linking to Duplex DNA', J. Am. Chem. Soc. 1991, 113, pp. 7765–7766.

Chang et al., 'Antisense Inhibition of ras p21 Expression That is Sensitive to a Point Mutation', Biochemistry (Am. Chem. Soc.), vol. 30, No. 34, Aug. 1991, pp. 8283–8286, (Aug. 27, 1991).

Nagatsugi et al., '2–Aminopurine Derivatives with C6–Substituted Olefin as Novel Cross–Linking Agents and the Synthesis of the Corresponding β–Phosphoramidite Precursors', *Tetrahedron*, vol. 53, No. 9, 1997, pp 3035–3044.

* cited by examiner

Primary Examiner—L. E. Crane
(74) Attorney, Agent, or Firm—Kendrew H. Colton; Fitch Even Tabin & Flannery

(57) ABSTRACT

There are provided 2-aminopurine derivatives represented by the following general formula (1):

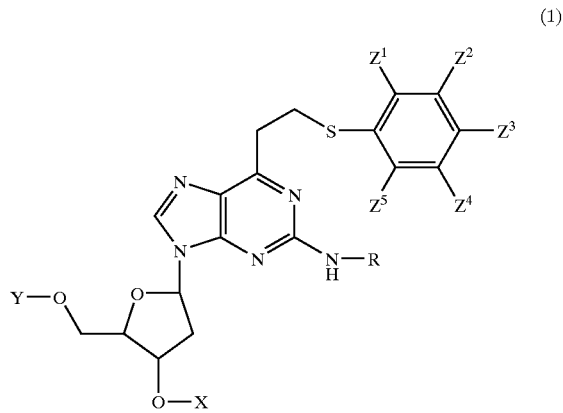

where R represents any species selected from the group consisting of hydrogen and acyl groups, X represents any species selected from the group consisting of phosphoramidite and oligonucleotides, Y represents any species selected from the group consisting of dimethyltrityl groups and oligonucleotides, and $Z^1$, $Z^2$, $Z^3$, $Z^4$ and $Z^5$ are the same or different and represent any species selected from the group consisting of hydrogen and hydroxyl, amino, lower alkyl, alkoxy, carboxyl and sulfonic acid groups, provided that $Z^1$, $Z^2$, $Z^3$, $Z^4$ and $Z^5$ are not all hydrogen, as well as gene expression-regulating compositions characterized by comprising the derivatives. By introducing the 2-aminopurine derivatives into oligonucleotides it is possible to achieve crosslinking reaction with high reactivity for target nucleic acids and notably high base sequence specificity.

17 Claims, 3 Drawing Sheets

SEQUENCE LISTING

<160> NUMBER OF SEQ ID NOS: 1

<210> SEQ ID NO 1
<211> LENGTH: 16
<212> TYPE: DNA
<213> ORGANISM: Artificial Sequence
<220> FEATURE:
<223> OTHER INFORMATION: DESCRIPTION OF ARTIFICIAL SEQUENCE: SYNTHETIC POLYNUCLEOTIDE

<400> SEQUENCE: 1 agaaggaga acaaag                                                    16

2-AMINOPURINE DERIVATIVES

CROSS-REFERENCED APPLICATIONS

This application is a national phase of International Application PCT/JP00/07748, filed Nov. 2, 2000, which designated the U.S. and that International Application was not published under PCT Article 21(2) in English.

TECHNICAL FIELD

The present invention relates to nucleic acid derivatives which are specifically reactive with target base sequences and to gene expression-regulating compositions comprising the derivatives. More specifically, it relates to nucleic acid derivatives which undergo crosslinking reaction(s) by forming complexes specifically with target base sequences or nucleic acid-binding proteins, and to gene expression-regulating compositions comprising the derivatives to allow specific expression regulation of genes.

BACKGROUND ART

Recent years have seen rapid progress in research on the use of drugs based on oligonucleotides, which are relatively low molecular nucleic acids. Particular attention is being directed toward antisense sequences that inhibit translation of genetic information by forming complementary double helixes with mRNA, triple-helix-forming oligonucleotides, or TFOs, that form triple helixes (triplexes) with chromosomal gene sequences and thereby inhibit transcription of genetic information, and decoys that inhibit transcription of genetic information by sequence-specific binding to nucleic acid-binding proteins such as transcription factors. However, the specific binding of such oligonucleotide drugs to their targets is known to be often weak and relatively prone to dissociation. A high demand therefore exists for development of new oligonucleotide drugs capable of binding more strongly to their targets, so that the oligonucleotides can be more effectively used as drugs.

The possibility of introducing point mutations into gene sequences by base sequence-specific crosslinking reaction has recently been noted (Woolf, T. et al., Nature Biotech. 1998, 16, 341), and there has been considerable focus on possible applications thereof. Numerous reports have therefore appeared with the goal of introducing reactive groups into oligonucleotides to achieve a target sequence-specific crosslinking reaction(s). Examples of such reactive groups include haloacetamides (Grant, K. et al., Biochemistry 1.996, 65, 12313), aziridines (Shaw, J. et al., J. Am. Chem. Soc. 1991, 113, 7765) and psoralen derivatives (Chang, E. et al., Biochemistry 1991, 30, 8283), which have been the subject of much investigation. However, non-specific bond formation tends to occur with these reactive groups and this has prevented achieving a truly target-specific crosslinking reaction(s).

While attempting to solve the problems mentioned above, the present inventors have previously found that the 2-amino-6-vinylpurine structure undergoes a base sequence-specific crosslinking reaction with cytidine (Nagatsugi, F. et al., Tetrahedron 1997, 53, 3035). However, the 2-amino-6-vinylpurine structure is not suitable because of its extremely high reactivity, which tends to produce a non-specific reaction(s) with the amino groups in proteins.

While attempting to solve this problem, the present inventors also found that it is useful to obtain phenylsulfide derivatives and phenylsulfoxide derivatives at the vinyl group of 2-amino-6-vinylpurine (Nagatsugi, F. et al., J. Am. Chem. Soc. 1999, 121, 6753). These derivatives are oxidized to produce the highly reactive 2-amino-6-vinylpurine after hydrogen bonding-driven formation of a complex with cytidine which has the target and complementary structure. The stability is high and non-specific reaction is minimized. In addition, through synthesis of an amidite reagent comprising the phenylsulfide derivative of the 2-amino-6-vinylpurine structure and its use as a reagent for oligonucleotide synthesis using a DNA synthesizer, it has become possible to introduce the phenylsulfide derivative of 2-amino-6-vinylpurine as a reactive group at any desired location of an oligonucleotide. Oxidation of the phenylsulfide derivative will then accomplish introduction of the phenylsulfoxide derivative of 2-amino-6-vinylpurine at any desired location of the oligonucleotide. However, the low reactivity of phenylsulfide derivative-containing oligonucleotides with their target nucleic acids remains a problem.

SUMMARY OF THE INVENTION

The present invention has been accomplished in light of the aforementioned circumstances of the prior art. An objective is to develop reactive groups with high reactivity and high base sequence specificity for target nucleic acids, and to provide 2-aminopurine derivatives that function as oligonucleotide precursors capable of undergoing a specific crosslinking reaction(s) with target nucleic acid base sequences when the above-mentioned reactive groups are introduced into oligonucleotides.

As a result of diligent research conducted with the aim of solving the aforementioned problems, the present inventors have completed the present invention. The present invention discovered that when preparing phenylsulfide derivatives at the vinyl group of 2-amino-6-vinylpurine, introducing an electron donor group, such as a hydrogen atom, hydroxyl group, amino group, methyl group, methoxy group, carboxyl group or sulfonic acid group, into the phenyl group proves quite useful in preventing non-specific reaction with nucleic acids other than the target nucleic acid.

Specifically, the invention provides 2-aminopurine derivatives represented by the following general formula (1):

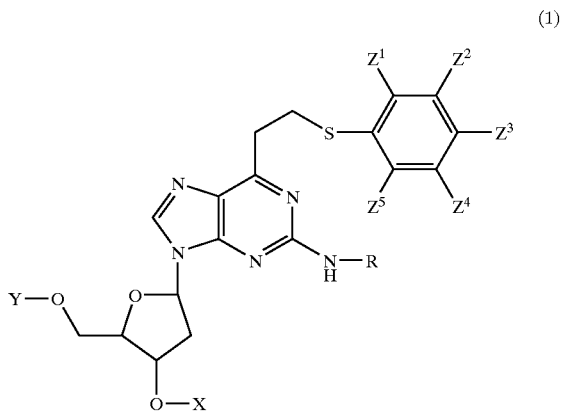

wherein R represents any substituent group selected from the group consisting of hydrogen and acyl groups, X represents any substituent group selected from the group consisting of a phosphoramidityl group and oligonucleotides, Y represents any substituent group selected from the group consisting of a dimethoxytrityl groups and oligonucleotides, and $Z^1$, $Z^2$, $Z^3$, $Z^4$ and $Z^5$ are the same or different and represent any substituent group selected from the group consisting of hydrogen, hydroxyl, amino, lower alkyl, alkoxy, carboxyl and sulfonic acid groups, provided that $Z^1$, $Z^2$, $Z^3$, $Z^4$ and $Z^5$ are not all hydrogen; and gene expression-regulating compositions comprising the aforementioned 2-aminopurine derivatives.

DETAILED DESCRIPTION OF THE INVENTION

Figure 1:
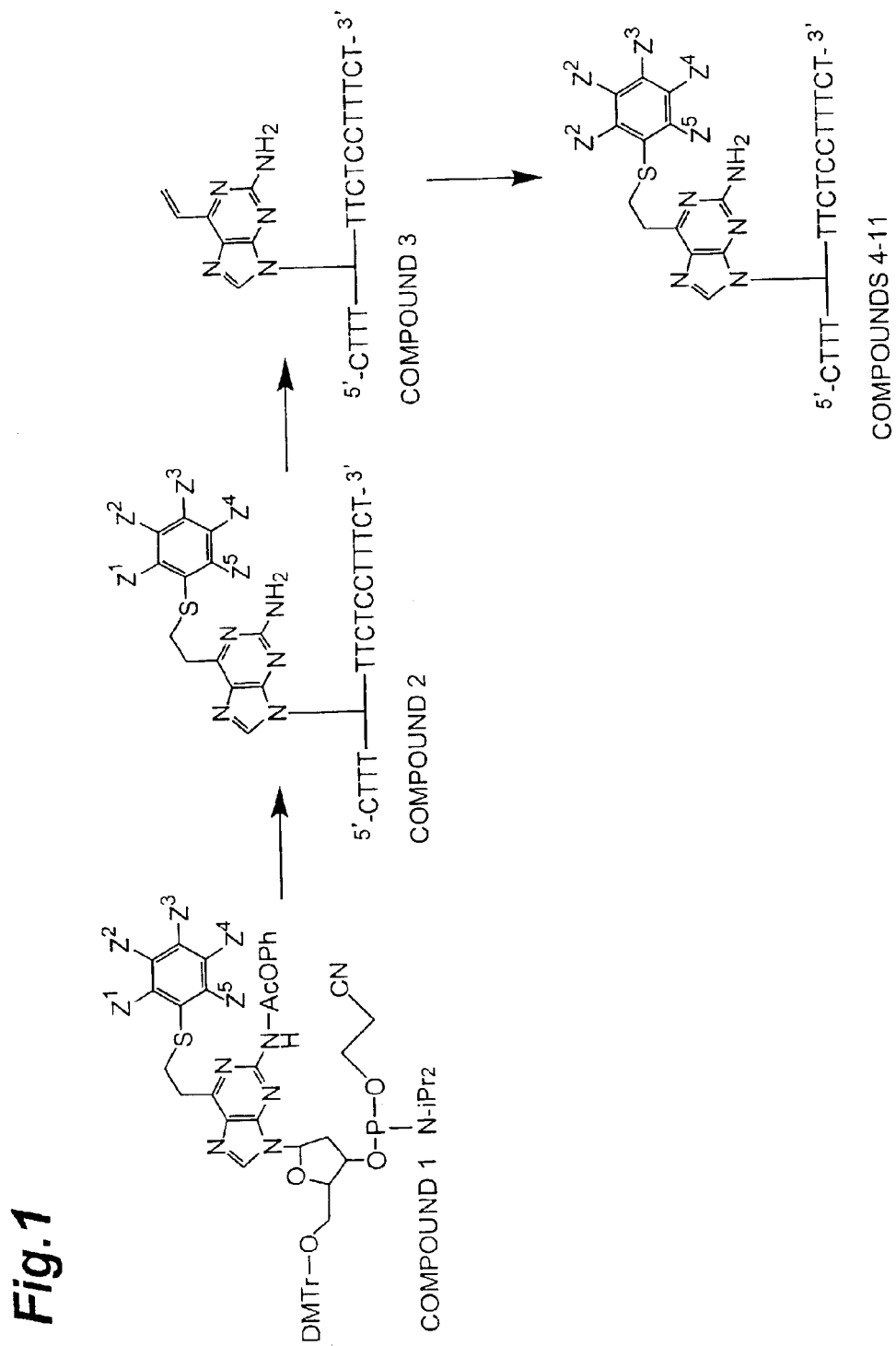
FIG. 1 is a diagram showing the synthesis pathway for the 2-aminopurine derivatives of the invention.
Figure 2:
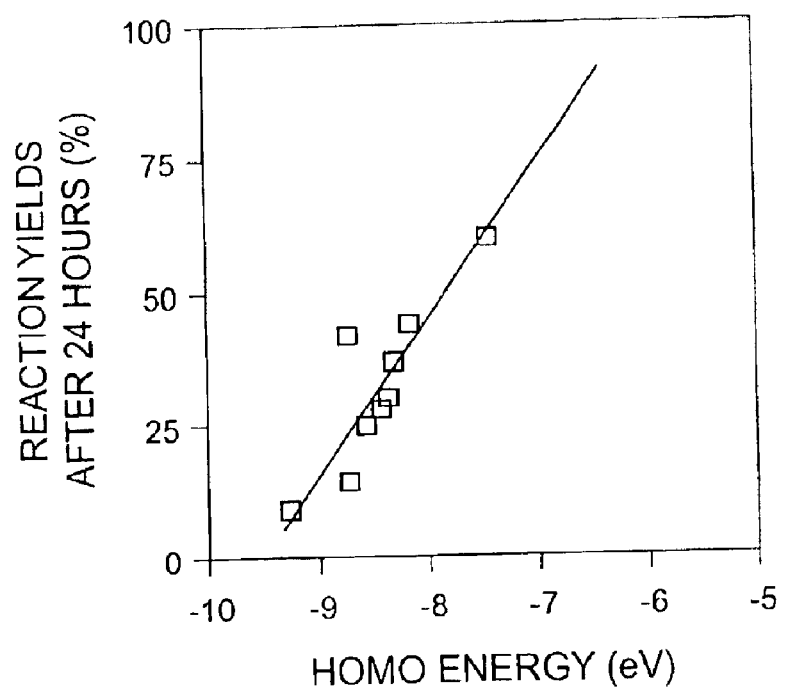
FIG. 2 is a graph showing the relationship between reaction efficiency of reactive nucleic acid and HOMO energy.

The construction and preferred modes of the invention will now be explained in detail.

The derivatives of the invention are 2-aminopurine derivatives that efficiently promote a crosslinking reaction (s) when forming complexes by hydrogen bonding with cytidine which has the complementary structure.

The reactive nucleic acids of the invention have a 2-aminopurine derivative structure, and specifically are 2-aminopurine derivatives represented by the following general formula (1):

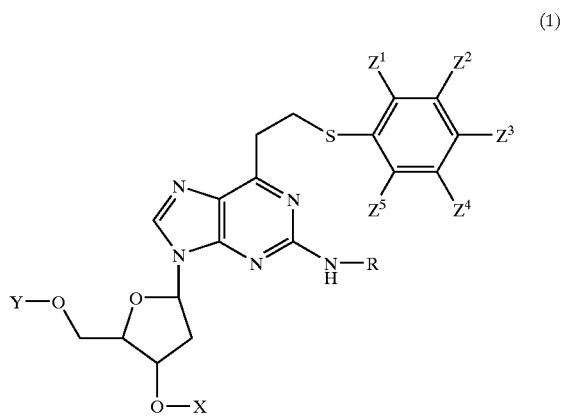

(1)

where R represents any species selected from the group consisting of hydrogen and acyl groups, X represents any species selected from the group consisting of phosphoramidite and oligonucleotides, Y represents any species selected from the group consisting of dimethyltrityl groups and oligonucleotides, and $Z^1$, $Z^2$, $Z^3$, $Z^4$ and $Z^5$ are the same or different and represent any species selected from the group consisting of hydrogen and hydroxyl, amino, lower alkyl, alkoxy, carboxyl and sulfonic acid groups, provided that $Z^1$, $Z^2$, $Z^3$, $Z^4$ and $Z^5$ are not all hydrogen.

Compounds having the 2-aminopurine derivative structure of the invention will be explained first.

R in general formula (1) represents hydrogen or an acyl group. As acyl groups there may be mentioned acetyl, phenoxyacetyl, formyl, propionyl, benzoyl and benzyloxycarbonyl, among which hydrogen and phenoxyacetyl are preferred.

X in general formula (1) represents a phosphoramidityl group (see FIG. 1) or an oligonucleotide. The oligonucleotide is not particularly restricted in terms of its base sequence or number of bases, and it may be selected as desired to be complementary to the target base sequence of the crosslinking reaction. However, it preferably has a number of bases suitable for hybridization with the target nucleic acid, and specifically, this is preferably 5–10,000 bases and more preferably 10–100 bases. When the number of bases is below this range the hybridization efficiency tend(s) to be reduced, and when the number of basis is above this range it tends to hybridize with non-specific nucleic acids.

Y in general formula (1) represents a dimethoxytrityl group or an oligonucleotide. Here, as well, the oligonucleotide is not particularly restricted in terms of its base sequence or number of bases, and may be selected as desired so as to have a base sequence and number of bases which are complementary to the target base sequence of the crosslinking reaction. However, it preferably has a number of bases suitable for hybridization with the target nucleic acid, and specifically, this is preferably 5–10,000, bases and more preferably 10–100 bases. When the number of bases is below this range the hybridization efficiency tends to be reduced, and when the number of bases is above this range it tends to hybridize with non-specific nucleic acids.

When X or Y in general formula (1) is an oligonucleotide, there are no particular restrictions on the number of 2-aminopurine derivatives bonded to the oligonucleotide, but the number will be at least 1 and is preferably no greater than one less than the total number of bases of the oligonucleotide.

There are also no restrictions on the base sequence of the oligonucleotide when X or Y in general formula (1) is an oligonucleotide, but it preferably has a function which forms a duplex or triplex with the base sequence complementary to the base sequence of the oligonucleotide.

Also, a cytidine structure is preferably present in the complementary base sequence as the target when the oligonucleotide forms the duplex or triplex with the complementary base sequence. That is, because the 2-amino-6-vinylpurine structure in the oligonucleotide tends to undergo a specific crosslinking reaction(s) with the cytidine structure, it will not produce a non-specific reaction with biological substances, thus allowing the oligonucleotide to bind to the target complementary base sequence. In such cases, the position of the cytidine structure in the target base sequence should complementarily match the position of the 2-aminopurine derivative.

In addition, the base sequence preferably codes for a given gene, which is preferably a gene with a sequence that specifically binds to a nucleic acid-binding protein such as a transcription factor. With such a gene as the target, the oligonucleotide containing the 2-aminopurine derivative of the invention will bind to the gene or nucleic acid-binding protein, thus allowing suppression of that gene's expression.

$Z^1$, $Z^2$, $Z^3$, $Z^4$ and $Z^5$ in general formula (1) are the same or different and each represents one selected from the group consisting of hydrogen, hydroxyl, amino, lower alkyl, alkoxy, carboxyl and sulfonic acid groups. These substituents $Z^1$, $Z^2$, $Z^3$, $Z^4$ and $Z^5$ may be the same or different, but the present invention does not encompasses compounds wherein all of these are hydrogen. When none of $Z^1$–$Z^5$ are the same, the reaction specificity for the target nucleic acid will tend to be higher as the number of identical functional groups increases. As lower alkyl groups there are preferred linear and branched alkyl groups of 1–5 carbons, such as methyl, ethyl, n-propyl, i-propyl, n-butyl, s-butyl and t-butyl. Such lower alkyl groups are preferably alkyl groups of 1–3 carbons, and methyl is most preferred. As alkoxy groups there may be mentioned methoxy, ethoxy, propoxy, butoxy and the like, among which methoxy is preferred.

The gene expression-regulating compositions of the invention will now be explained.

A gene expression-regulating composition of the invention comprises a 2-aminopurine derivative represented by general formula (1) above, where X and/or Y in the compound of general formula (1) are preferably oligonucleotides.

The gene expression-regulating composition comprising a 2-aminopurine derivative according to the invention may also contain a pharmacologically acceptable salt of the compound represented by general formula (1). A pharmacologically acceptable salt is a salt that does not affect biological function when administered, and it is obtained by adding a publicly known acid or base to the compound represented by general formula (1). Pharmacologically acceptable acid-addition salts include examples such as inorganic acid salts such as hydrochloric acid salts, nitric acid salts, and phosphoric acid salts, and organic acid salts such as acetic acid salts, lactic acid salts, oxalic acid salts, citric acid salts, tartaric acid salts and p-toluenesulfonic acid salts. Pharmacologically acceptable base-addition salts include such specific examples as inorganic salts such as sodium, potassium, calcium, aluminum and ammonium salts, and organic amine salts.

Other compounds may also be added to the gene expression-regulating composition. Examples of other compounds include cationic proteins or peptides, cationic synthetic polymers, cationic liposomes, cationic emulsions and cationic lipids.

The amount of the 2-aminopurine derivative represented by general formula (1) or its salt which is contained in the gene expression-regulating composition of the invention will differ depending on the drug form but is preferably 0.00001–100 wt % with respect to the total of the gene expression-regulating composition.

The gene expression-regulating composition of the invention may also contain, in addition to the 2-aminopurine derivative, also binders, inclusion agents, excipients, disintegrators and the like.

An exemplary method of using the gene expression-regulating composition comprising the 2-aminopurine derivative-containing oligonucleotide, comprises introducing or injecting the composition into a cultured cell system to allow control of expression of a desired gene, thus making it possible to study control of expression or transcription in relation to the gene function.

Another exemplary method of using the gene expression-regulating composition comprising the synthesized 2-aminopurine derivative-containing oligonucleotide, be comprises directly administering the composition into the body of control expression of a desired gene, thus allowing its use as a therapeutic agent for diseases causes by anomalies in expression of that gene or changes in its degree of expression.

An embodiment of a process for producing the 2-aminopurine derivatives of the invention will now be explained.

The production process for the 2-aminopurine derivatives of the invention comprises, for example, (i) a first step of introducing a thiophenol at the vinyl group of a 2-amino-6-vinylpurine derivative represented by general formula (2):

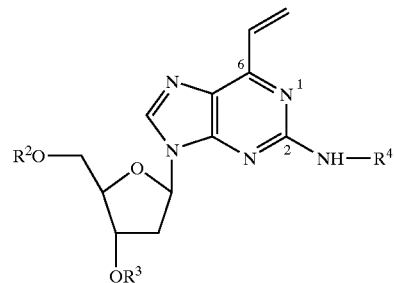

wherein $R^2$ and $R^3$ are the same or different and represent silyl groups, and $R^4$ represents hydrogen or an acyl group; and (ii) a second step of introducing a trityl group at the $R^2$ and introducing a phosphoramidityl group at the $R^3$ of the compound obtained by the first step. An electron donor group such as a hydroxyl group, an amino group, a methyl group, a methoxy group, a carboxyl group or a sulfonic acid group is preferably introduced into the thiophenol group introduced in the first step. This will prevent non-specific reaction with nucleic acids other than the target nucleic acid when the 2-aminopurine derivative of the invention binds to the target nucleic acid.

$R^2$ and $R^3$ in general formula (2) may be optionally substituted, and as a specific group there may be mentioned tert-butyldimethylsilyl. As acyl groups for $R^4$ in general formula (2) there may be mentioned acetyl, phenoxyacetyl, formyl, propionyl, benzoyl and benzyloxycarbonyl. $R^4$ in general formula (2) is preferably hydrogen or phenoxyacetyl.

In order to introduce the thiophenol or electron donor group-modified thiophenol at the vinyl group of the 2-amino-6-vinylpurine derivative, the thiophenol or electron donor group-modified thiophenol may be added to a solution containing the 2-amino-6-vinylpurine, and mixed therewith. There are no particular restrictions on the reaction temperature for this production process. The reaction may be carried out at room temperature. If the reaction is carried out at room temperature, the mixture is preferably stirred for a period from about 30 minutes to 3 hours.

To introduce the trityl group at $R^2$ of the compound represented by general formula (2), for example, the compound obtained by the first step according to the invention and dimethoxytrityl chloride may be dissolved in pyridine, and the solution stirred in the presence of a molecular sieve. There are no particular restrictions on the reaction temperature and reaction time. Stirring at 0° C. for a period from about 30 minutes to 3 hours is preferred. A tritylated form of the compound represented by general formula (2) above may thus be obtained.

A phosphoramidtyl group may be introduced at $R^3$ of the compound represented by general formula (2) by, for example, adding 2-cyanoethyl-N,N-diisopropylchlorophosphoramidite to a solution of the aforementioned tritylated compound in dichloromethane, and mixing, the solution. There are no particular restrictions on the reaction temperature and reaction time. Stirring at 0° C. for a period from about 30 minutes to 3 hours is preferred.

The compound obtained in this manner is a compound having phosphoramidityl as X and dimethoxytrityl as Y in general formula (1).

The process for production of the 2-aminopurine derivative of the invention may also further include, in addition to the 2-aminopurine derivative production steps described above, a step of bonding amidite reagents selected from the group consisting of adenine, guanine, cytosine, thymine and the compound obtained by the aforementioned 2-aminopurine derivative production process, in the prescribed order to produce the desired base sequence.

The compound obtained by the aforementioned 2-aminopurine derivative production process is provided with the oligonucleotide synthesizing materials together with commercially available adenine, guanine, cytosine and thymine, and linked using a commercially available DNA synthesizer to produce the desired base sequence.

The compound obtained in this manner is a compound wherein either or both of X and Y in general formula (1) are oligonucleotides.

A concrete example of a process for production of the 2-aminopurine derivatives of the invention will now be explained.

A phosphoramidite reagent wherein R=phenoxyacetyl, X=phosphoramidityl and Y=dimethoxytrityl in general formula (1) is produced by introducing a thiophenol or an electron donor-modified thiophenol at the vinyl group of 2-amino-9-(3,5-di-O-t-butyldimethylsilyl-2-deoxy-D-ribofuranosyl)-6-vinylpurine, protecting the amino group with phenoxyacetyl chloride, and then deprotecting the 3- and 5-positions of the 2-deoxy-D-ribofuranosyl and introducing trityl at the 3-position and phosphoramidityl at the 5-position. This allows introduction of a reactive base at any desired position of the oligonucleotide with, for example, a DNA synthesizer by coupling reaction of the phosphoramidite reagent.

For a reactive oligonucleotide wherein R=hydrogen, X=oligonucleotide and Y=oligonucleotide in general formula (1), a thiophenol is introduced at the vinyl group of 2-amino-9-(3,5-di-O-t-butyldimethylsilyl-2-deoxy-D-ribofuranosyl)-6-vinylpurine, the amino group is protected with phenoxyacetyl chloride, and then the 3- and 5-positions of the 2-deoxy-D-ribofuranosyl are deprotected and trityl is introduced at the 3-position and phosphoramidityl at the 5-position. The phosphoramidite reagent produced thereby is used simultaneously with the respective amidite reagents for adenine, guanine, cytosine and thymine with a DNA synthesizer by coupling reaction of the phosphoramidite reagent, and electron donor group-modified thiophenol is then introduced at the deprotected vinyl group. Alternatively, an electron donor group-modified thiophenol is introduced at the vinyl group of 2-amino-9-(3,5-di-O-t-butyldimethylsilyl-2-deoxy-D-ribofuranosyl)-6-vinylpurine, the amino group is protected with phenoxyacetyl chloride, and then the 3- and 5-positions of the 2-deoxy-D-ribofuranosyl are deprotected and trityl is introduced at the 3-position and phosphoramidityl at the 5-position to produce a phosphoramidite reagent which is then used simultaneously with the respective amidite reagents for adenine, guanine, cytosine and thymine with a DNA synthesizer by coupling reaction of the phosphoramidite reagent. Here, the base sequence of the oligonucleotides and the number and positions of the reactive bases of the oligonucleotides may be set as desired.

As explained above, 2-amino-6-vinylpurine derivatives have a property of undergoing a crosslinking reaction(s) with cytidine, but have had the drawbacks of very high reactivity, tending to form non-specific bonds in the body. However, it is possible to achieve a crosslinking reaction with a target nucleic acid base sequence(s) with an extremely high degree of specificity by introducing an electron donor group-containing sulfide derivatives or sulfone derivatives at the vinyl groups of 2-amino-6-vinylpurine derivatives.

EXAMPLES

The present invention will now be explained in detail by way of examples, with the understanding that the invention is in no way limited thereby.

Comparative Example 1
Synthesis of Reactive Oligonucleotide (Compound 2)

A 2-aminopurine derivative amidite reagent (Compound 1) was synthesized according to the protocol of Nagatsugi et al. (J. Am. Chem. Soc. 1999, 121, 6753). The oligonucleotide synthesis was carried out according to an established procedure, using a Cyclon Plus DNA-Synthesizer (Milligen/Biosearch) and using commercially available amidite reagents and Compound 1 on a 1.0 $\mu$mol scale. After completion of synthesis, the protecting group at the 5' end of the oligonucleotide was removed using a 0.1 N NaOH aqueous solution (2.0 mL) and the mixture was neutralized immediately with acetic acid. The oligonucleotide was purified by HPLC (COSMOSIL 5C18-MS 10×250 mm by Nacalai Tesque; mobile phase: 0.1 M TEA buffer solution with 10–40% acetonitrile concentration gradient, flow rate: 4.0 mL/min). The purified oligonucleotide was used after deprotection with a 10% acetic acid aqueous solution and further purification. The mass spectral data for the obtained compound were as follows:

MS(m/z): 4875.15 (M−1, calcd. 4873.84).

Production Example 1
Synthesis of Oligonucleotide (Compound 3: Vinyl Compound)

A monomagnesium perphthalate aqueous solution (660 $\mu$M) adjusted to a pH of 10 with a 0.01 M NaOH aqueous solution was added to an aqueous solution of Compound 2 (200 $\mu$M) and the mixture was allowed to stand at room temperature for 30 minutes. Next, a 4 N NaOH aqueous solution (5 $\mu$L) was added, and the mixture was allowed to stand at room temperature for 30 more minutes. The reaction solution was dialyzed overnight against a phosphate buffer solution (0.5M–1.0M) and then subjected to HPLC (COSMOSIL 5C18-MS 4.6×25 by Nacalai Tesque; mobile phase: A: 0.1 M TEAA, B: $CH_3CN$ with 10–30% concentration gradient/20 min, flow rate: 1.0 mL/min), to obtain Compound 3 (retention time: 13.0 min). The mass spectral data for the obtained compound were as follows:

MS(m/z): 4761.10 (M−1, calcd. 4763.82).

Comparative Example 2
Synthesis of Reactive Oligonucleotide (Compound 4: 4-$NO_2$ Compound)

After adding 4-nitrobenzenethiol (5–10 equivalents) to Compound 3 (5 nmol in 50 $\mu$L $H_2O$) and allowing the mixture to stand for 30 minutes, it was separated and purified by HPLC (COSMOSIL 5C18-MS 4.6×250 mm by Nacalai Tesque; mobile phase: 0.1 M TEA buffer solution with 10–30% acetonitrile/20 min concentration gradient), to obtain Compound 4. The mass spectral data for the obtained compound were as follows:

MS(m/z): 4919.1 (M−1, calcd. 4819.8).

Comparative Example 3
Synthesis of Reactive Oligonucleotide (Compound 5: 4-Br Compound)

After adding 4-bromobenzenethiol (5–10 equivalents) to Compound 3 (5 nmol in 50 $\mu$L $H_2O$) and allowing the mixture to stand for 30 minutes, it was separated and purified by HPLC (COSMOSIL 5C18-MS 4.6×250 mm by Nacalai Tesque; mobile phase: 0.1 M TEA buffer solution with 10–30% acetonitrile/20 min concentration gradient), to obtain Compound 5. The mass spectral data for the obtained compound were as follows:

MS(m/z): 4951.9 (M−1, calcd. 4952.7).

Example 1

Synthesis of reactive oligonucleotide (Compound 6: 4-OH compound)

After adding 4-hydroxybenzenethiol (5–10 equivalents) to Compound 3 (5 nmol in 50 μL $H_2O$) and allowing the mixture to stand for 30 minutes, it was separated and purified by HPLC (COSMOSIL 5C18-MS 4.6×250 mm by Nacalai Tesque; mobile phase: 0.1 M TEA buffer solution with 10–30% acetonitrile/20 min concentration gradient), to obtain Compound 6. The mass spectral data for the obtained compound were as follows:

MS(m/z): 4891.8 (M−1, calcd. 4890.8).

Example 2

Synthesis of Reactive Oligonucleotide (Compound 7: 4-$NH_2$ Compound)

After adding 4-aminobenzenethiol (5–10 equivalents) to Compound 3 (5 nmol in 50 μL $H_2O$) and allowing the mixture to stand for 30 minutes, it was separated and purified by HPLC (COSMOSIL 5C18-MS 4.6×250 mm by Nacalai Tesque; mobile phase: 0.1 M TEA buffer solution with 10–30% acetonitrile/20 min concentration gradient), to obtain Compound 7. The mass spectral data for the obtained compound were as follows:

MS(m/z): 4886.7 (M−1, calcd. 4886.7).

Example 3

Synthesis of reactive oligonucleotide (Compound 8: 2,4-$Me_2$ compound)

After adding 2,4-dimethylbenzenethiol (5–10 equivalents) to Compound 3 (5 nmol in 50 μL $H_2O$) and allowing the mixture to stand for 30 minutes, it was separated and purified by HPLC (COSMOSIL 5C18-MS 4.6×250 mm by Nacalai Tesque; mobile phase: 0.1 M TEA buffer solution with 10–30% acetonitrile/20 min concentration gradient), to obtain Compound 8. The mass spectral data for the obtained compound were as follows:

MS(m/z): 4900.3 (M−1, calcd. 4902.8).

Example 4

Synthesis of Reactive Oligonucleotide (Compound 9: 3,4-$(MeO)_2$ Compound)

3,4-dimethoxyphenylsulfonyl chloride (2.3 mmol) was dissolved in acetone (60 mL), and then NaI (3.4 g, 23 mmol) and fluoroacetic anhydride (1.45 mL, 6.9 mmol) were added and the mixture was stirred at room temperature for one hour. The reaction solution was concentrated, water was added, extraction was performed with ether and the organic layer was further washed with aqueous sodium thiosulfate, water and saturated saline. After drying over magnesium sulfate and vacuum concentration, the residue was purified with a silica gel column (hexane) to obtain 3,4-dimethoxyphenyldisulfide as a light yellow crystalline compound (58% yield). The NMR and mass spectral data for the obtained compound were as follows:

1H-NMR $(CDCl_3)\sigma$: 7.07–7.01 (4H, m), 6.79 (2H, d, J=8.25 Hz), 3.87 (6H, s), 3.83 (6H, s)

FABMS(m/z): 338 (M+).

After dissolving the 3,4-dimethoxyphenyldisulfide synthesized by the aforementioned method (6.6 μmol) in ethanol (300 μL), $NaBH_4$ (2 mg, 6.6 μmol) was added and the mixture was allowed to stand for 24 hours. After adding 4 μL of the reaction solution to Compound 3 (1.5 nmol, 30 μL) and allowing the mixture to stand for 30 minutes, it was separated and purified by HPLC to obtain Compound 9. The mass spectral data for the obtained compound were as follows:

MS(m/z): 4934.9 (M−1, calcd. 4934.9).

Example 5

Synthesis of Reactive Oligonucleotide (Compound 10: 2,4,6-($Me_3$ Compound)

2,4,6-trimethylphenylsulfonyl chloride (500 mg, 2.3 mmol) was dissolved in acetone (60 mL), and then NaI (3.4 g, 23 mmol) and fluoroacetic anhydride (1.45 mL, 6.9 mmol) were added and the mixture was stirred at room temperature for one hour. The reaction solution was concentrated, water was added, extraction was performed with ether and the organic layer was further washed with aqueous sodium thiosulfate, water and saturated saline. After drying over magnesium sulfate and vacuum concentration, the residue was purified with a silica gel column (hexane) to obtain 2,4,6-trimethylphenyldisulfide as a light yellow crystalline compound (231 mg, 0.76 mmol, 67% yield). The NMR and mass spectral data for the obtained compound were as follows:

$^1$H-NMR $(CDCl_3)_6$: 6.83 (4H, s), 2.25 (6H, s), 2.20 (12H, S)

FABMS(m/z): 302 (M+).

Melting point: 118–119° C.

After dissolving the 2,4,6-trimethylphenyldisulfide synthesized by the aforementioned method (6.6 μmol) in ethanol (300 μL), $NaBH_4$ (2 mg, 6.6 μmol) was added and the mixture was allowed to stand for 24 hours. After adding 4 μL of the reaction solution to Compound 3 (1.5 nmol, 30 μL) and allowing the mixture to stand for 30 minutes, it was separated and purified by HPLC to obtain Compound 10. The mass spectral data for the obtained compound were as follows:

MS(m/z): 4919.8 (M−1, calcd. 4916.8).

Example 6

Synthesis of Reactive Oligonucleotide (Compound 11: 2-COOH Compound)

After adding 2-carboxybenzenethiol (5–10 equivalents) to Compound 3 (5 nmol in 50 μL $H_2O$) and allowing the mixture to stand for 30 minutes, it was separated and purified by HPLC (COSMOSIL 5C18-MS 4.6×250 mm by Nacalai Tesque; mobile phase: 0.1 M TEA buffer solution with 10–30% acetonitrile/20 min concentration gradient), to obtain Compound 11. The mass spectral data for the obtained compound were as follows. The synthesis pathway for the obtained compound is shown in FIG. 1.

MS(m/z): 4819.2 (M−1, calcd. 4818.8).

Example 7 and Comparative Example 4

Crosslinking Experiment

A crosslinking experiment using reactive oligonucleotides was carried out in the following manner following the protocol of Nagatsugi et al. (J. Am. Chem. Soc. 1999, 121, 6753).

A mixture comprising 20 pM of an oligonucleotide having a sequence complementary to the reactive oligonucleotide (3'-GAAA-C-AAGAGGAAAGA-5': SEQ. ID. No. 1), [γ-$^{32}$P]ATP (ICN; 4500 Ci/mmol) and T4 polynucleotide kinase (Takara Shuzo) was reacted at 37° C. for one hour, and then 30 μL of a 0.5 M Tris-EDTA buffer solution (100 mM NaCl) was added and the mixture was heated at 60° C. for 5 minutes. The 5'-end $^{32}$P_labeled oligonucleotide was purified with an ion-exchange column and its concentration was measured by UV.

Oligonucleotides having reactive bases introduced therein (Compounds 2, 4, 5, 6, 7, 8, 9, 10 and 11: 7 μM) were each dissolved in 50 mM 3-(N-morpholino)propanesulfonic acid buffer solution (0.1 M NaCl, pH 5.0), and then the aforementioned 5'-end $^{32}$P_labeled oligonucleotide (2×10$^4$ cpm) and a non-labeled oligonucleotide (3 μM) having the same sequence as each of these oligonucleotides was added. After then heating at 45° C. for 10 minutes, the mixture was allowed to stand at room temperature for one hour. The reaction was conducted at 33° C., and after 24 hours a stop solution and pigment (95% formamide, 20 mM EDTA, 0.05% Xylenecyanol, 0.05% Bromophenol blue) were added and heating was continued at 95° C. for 5 minutes to suspend the reaction. The reaction solution was subjected to electrophoresis (400 V, 1 hour) with 20% polyacrylamide gel containing 7 M urea. The gel was analyzed using a BAS2000 (Fuji Film).

Figure 3:
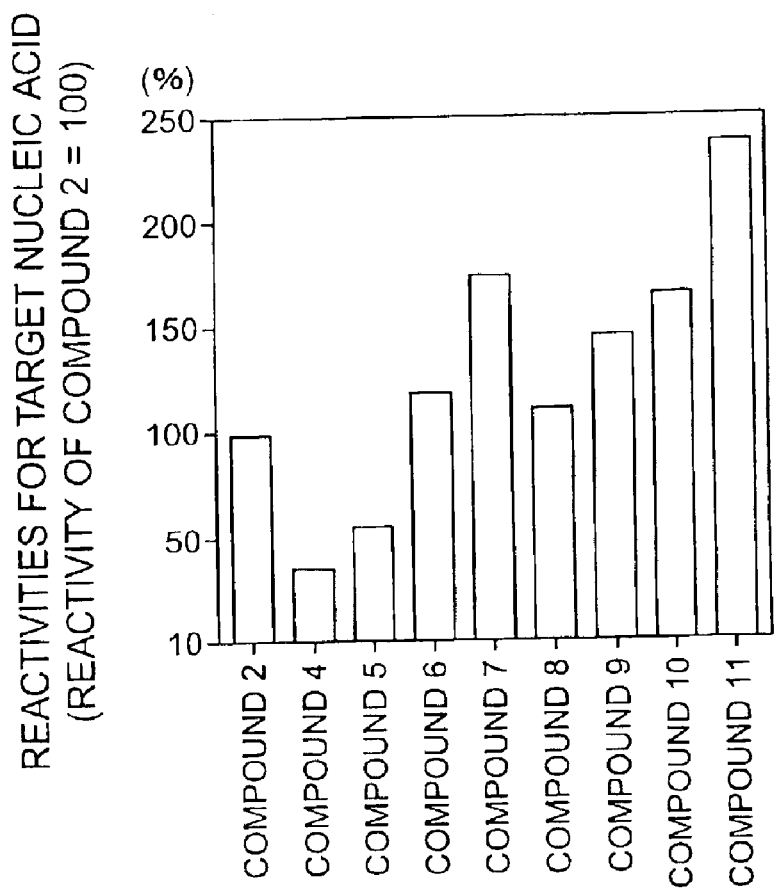
FIG. 3 is a graph showing the reactivities of different compounds where the reactivity of Compound 2 for its target nucleic acid is defined as 100.

As a result, Compounds 4 and 5 which had electron attracting groups introduced at the phenyl group exhibited a reduction in reactivity with the target nucleic acid compared to Compound 2 which had no substituent introduced. On the other hand, Compounds 6, 7, 8, 9, 10 and 11 which had electron donor groups introduced at the phenyl group exhibited greater reactivity for the target nucleic acid compared to Compound 2 which had no substituent introduced. This indicated that the reactive bases synthesized here had increased reactivity for the target nucleic acid by introduction of electron donor groups at the phenyl group. The results are shown in Table 1, while FIG. 3 shows the activities of the compounds where the reactivity of Compound 2 for the target nucleic acid is defined as 100.

TABLE 1

| Compounds | Reactivity with target nucleic acid (%) |
|---|---|
| Compound 2: $Z^1, Z^2, Z^3, Z^4, Z^5$ = H | 25 |
| Compound 4: $Z^1, Z^2, Z^4, Z^5$ = H, $Z^3$ = $NO_2$ | 9 |
| Compound 5: $Z^1, Z^2, Z^4, Z^5$ = H, $Z^3$ = Br | 14 |
| Compound 6: $Z^1, Z^2, Z^4, Z^5$ = H, $Z^3$ = OH | 30 |
| Compound 7: $Z^1, Z^2, Z^4, Z^5$ = H, $Z^3$ = $NH_2$ | 44 |
| Compound 8: $Z^2, Z^4, Z^5$ = H, $Z^1, Z^3$ = $CH_3$ | 28 |
| Compound 9: $Z^1, Z^4, Z^5$ = H, $Z^2, Z^3$ = $OCH_3$ | 37 |
| Compound 10: $Z^2, Z^4$ = H, $Z^1, Z^3, Z^5$ = $CH_3$ | 42 |
| Compound 11: $Z^2, Z^3, Z^4, Z^5$ = H, $Z^1$ = COOH | 60 |

Plotting the reaction yields against HOMO energy calculated by MOPAC6 (PM3) for this reaction system revealed a linear relationship between them. This indicated that crosslinking reaction is proportional to HOMO energy, thus suggesting that the electron donor-introduced phenylsulfide modified 2-amino-6-vinylpurine derivatives are activated upon oxidation reaction within DNA.

The above results demonstrate that the electron donor-introduced phenylsulfide modified 2-amino-6-vinylpurine derivatives synthesized for this experiment are more chemically stable than previously reported phenylsulfoxide-modified 2-amino-6-vinylpurine derivatives, and are specifically activated in an oxidizing atmosphere.

INDUSTRIAL APPLICABILITY

As explained above, the 2-aminopurine derivatives of the present invention provide reactive groups which give the derivatives high reactivity and high base sequence specificity for target nucleic acids. It is thereby possible to obtain 2-aminopurine derivatives that function as oligonucleotide precursors that are capable of undergoing a very highly specific crosslinking reaction(s) with target nucleic acid base sequences when the reactive groups are introduced into the oligonucleotides.

We claim:
1. A 2-aminopurine derivative represented by the following general formula (1):

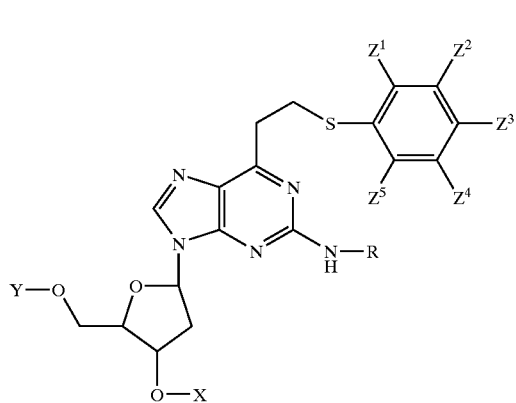

where R represents any substituent group selected from the group consisting of hydrogen and acyl groups, X represents any substituent group selected from the group consisting of a phosphoramidityl group and oligonucleotides, Y represents any substituent group selected from the group consisting of a dimethoxytrityl group and oligonucleotides, and $Z^1$, $Z^2$, $Z^3$, $Z^4$ and $Z^5$ are the same or different and represent any substituent group selected from the group consisting of hydrogen, hydroxyl, amino, lower alkyl, alkoxy, carboxyl and sulfonic acid groups, provided that $Z^1$, $Z^2$, $Z^3$, $Z^4$ and $Z^5$ are not all hydrogen, or a pharmaceutically-acceptable salt thereof.

2. The 2-aminopurine derivative according to claim 1, wherein said lower alkyl group is methyl and said alkoxy group is methoxy.

3. The 2-aminopurine derivative according to claim 1, wherein at least one of X or Y is an oligonucleotide.

4. The 2-aminopurine derivative according to claim 1, wherein X represents a phosphoroamidityl group and Y represents an oligonucleotide.

5. The 2-aminopurine derivative according to claim 1, wherein X is an oligonucleotide and Y represents a oligonucleotide.

6. The 2-aminopurine derivative according to any one of claims 1 and 4–6, wherein said oligonucleotide is 5–10,000 bases in length.

7. The 2-aminopurine derivative according to claim 6, wherein said oligonucleotide is 10–100 bases in length.

8. The 2-aminopurine derivative according to claim 1, wherein said lower alkyl is an alkyl group having of 1–5 carbon atoms.

9. The 2-aminopurine derivative according to claim 1, wherein said lower alkyl is selected from the group consisting of methyl, ethyl, n-propyl, i-propyl, n-butyl, s-butyl and t-butyl.

10. The 2-aminopurine derivative according to claim 1, wherein said lower alkyl group is an alkyl group having 1–3 carbon atoms.

11. The 2-aminopurine derivative according to claim 1, wherein said alkoxy group is selected from the group consisting of methoxy, ethoxy, propoxy and butoxy.

12. A composition comprising the 2-aminopurine derivative according to any one of claim 1, 2, 3, 5, 4, 8, 9 or 11, wherein said composition comprises at least 0.00001 wt %, based on the total amount of said composition, of said 2-aminopurine derivative or pharmaceutically acceptable salt thereof; and at least one member selected from the group consisting of a pharmaceutically acceptable binder, an inclusion agent, an excipient and a disintegrator.

13. A composition according to claim 12, wherein said oligonucleotide is 5–10,000 bases in length.

14. The composition according to claim 13, wherein said oligonucleotide is 10–100 bases in length.

15. A composition comprising the 2-aminopurine derivative according to any one of claim 1, 2, 3, 4, 5, 8, 9, 10 or 11, wherein said composition comprises at least 0.00001 wt. % of said 2-aminopurine derivative; and said composition further comprises a cationic protein or peptide, a cationic synthetic polymer, a cationic liposome, or a cationic lipid.

16. The composition according to claim 15, wherein said oligonucleotide is 5–10,000 bases in length.

17. The composition according to claim 16, wherein said olignucleotide is 10–100 bases in length.

* * * * *